United States Patent [19]

Snipes et al.

[11] Patent Number: 5,082,655
[45] Date of Patent: * Jan. 21, 1992

[54] PHARMACEUTICAL COMPOSITION FOR DRUGS SUBJECT TO SUPERCOOLING

[75] Inventors: Wallace C. Snipes, Pine Grove Mills; Neena Agarwala, University Park, both of Pa.

[73] Assignee: Zetachron, Inc., State College, Pa.

[*] Notice: The portion of the term of this patent subsequent to Feb. 21, 2006 has been disclaimed.

[21] Appl. No.: 311,960

[22] Filed: Feb. 17, 1989

Related U.S. Application Data

[63] Continuation-in-part of Ser. No. 918,273, Oct. 14, 1986, Pat. No. 4,806,337, which is a continuation-in-part of Ser. No. 633,604, Jul. 23, 1984, Pat. No. 4,629,621.

[51] Int. Cl.$^5$ .................. A61K 31/74; A61K 9/22; A01N 25/08; A01N 25/34
[52] U.S. Cl. .................. 424/386; 424/408; 424/426; 424/457; 424/462; 424/484; 71/64.11; 71/65
[58] Field of Search .............. 71/65, 64.11; 424/457, 424/465, 468, 469, 408, 78, 426, 428, 458, 459, 462, 464, 474, 475, 476, 482, 484, 486, 489, 490, 497, 498, 501, 502; 514/772, 782

[56] References Cited

U.S. PATENT DOCUMENTS

| | | | |
|---|---|---|---|
| 2,975,099 | 3/1961 | Goyan | 514/39 |
| 3,039,933 | 6/1962 | Goldman | 424/469 |
| 3,374,146 | 3/1968 | Blicharz | 424/452 |
| 3,511,914 | 5/1970 | Wolkoff et al. | 514/772 |
| 3,670,065 | 6/1972 | Eriksson | 264/131 |
| 3,832,460 | 8/1974 | Kosti | 424/54 |
| 3,947,573 | 3/1976 | Rankin | 424/80 |
| 4,151,273 | 4/1979 | Riegelman et al. | 424/78 |
| 4,264,573 | 4/1981 | Powell et al. | 424/19 |
| 4,624,849 | 11/1986 | Toogood | 424/78 |
| 4,806,337 | 2/1989 | Soupes et al. | 71/65 |

FOREIGN PATENT DOCUMENTS

| | | |
|---|---|---|
| 97507 | 1/1984 | European Pat. Off. |
| 287292 | 4/1914 | Fed. Rep. of Germany |
| 2501808 | 7/1975 | Fed. Rep. of Germany |
| 3217071 | 11/1983 | Fed. Rep. of Germany |
| 81-115726 | 10/1982 | Japan |
| 82-167911 | 12/1982 | Japan |
| 82-206612 | 10/1984 | Japan |
| 967610 | 8/1964 | United Kingdom |
| 1502441 | 3/1978 | United Kingdom |

OTHER PUBLICATIONS

"Carbowax TM Polyethylene Glycols for Pharmaceuticals and Cosmetics", Union Carbide Chemicals Co. (PTO Scientific Library, Received 1960).

Primary Examiner—Thurman K. Page
Assistant Examiner—Carlos Azpuru
Attorney, Agent, or Firm—Vorys, Sater, Seymour & Pease

[57] ABSTRACT

A sustained release composition for releasing a biologically active compound into an aqueous liquid environment comprises a biologically active compound dispersed in a matrix which progressively erodes in contact with a liquid environment, the matrix having a melting point below the melting point of the biologically active compound, and the matrix comprising a mixture of a.) 5% to 100% by weight of a solid water-dispersible polyether diol having a molecular weight from about 1000 to about 20,000, selected from the group consisting of polyethylene glycols and polyethylene oxide-polypropylene oxide block copolymers, and b.) 95 to 0% by weight of an erosion rate modifier which is an amphiphilic compound insoluble in the aqueous liquid.

Dosage forms comprising the sustained release composition are prepared by molding, particularly by injection molding.

59 Claims, No Drawings

PHARMACEUTICAL COMPOSITION FOR DRUGS SUBJECT TO SUPERCOOLING

CROSS-REFERENCE TO RELATED APPLICATIONS

This application is a continuation-in-part application of U.S. patent application No. 06/918,273, filed Oct. 14, 1986, which is a continuation-in-part of U.S. patent application No. 06/633,604, filed July 23, 1984, now U.S. Pat. No. 4,629,621.

BACKGROUND OF THE INVENTION

1. Field of the Invention

This invention relates to erodible compositions suitable for pharmaceutical excipients and more particularly to erodible compositions suitable for use as excipients for drugs which are subject to supercooling.

2. Description of the Prior Art

In chemotherapy of diseases it is frequently desirable to maintain the concentration of the therapeutic drug at a relatively constant level in the blood or organ being treated. One method for achieving this goal is to administer the drug continuously at a rate which balances its rate of metabolism and/or excretion. In a hospital environment this goal can be attained by intravenously administering a drug, but outside of such an environment this method of administration is impractical in the great majority of cases. Consequently, the most common method of administering a drug is orally, in the form of tablets, capsules, and the like, which preferably have sustained release characteristics. The drug released therefrom is usually absorbed from the gastrointestinal tract and reaches the target organ via the blood stream.

Among the various types of sustained release dosage forms which have been developed are erodible matrices, i.e., dosage forms wherein the drug is entrapped in a matrix which upon ingestion gradually decomposes in the intestinal fluid thereby releasing the drug for absorption. An example of such a dosage form is found in Schmitt, U.S. Pat. No. 4,346,709, wherein the device comprises a drug dispersed in a bioerodible polymer which is a poly(orthoester) or a poly(orthocarbonate) containing an erosion rate modifier. The erosion rate modifiers of Schmitt are mono- and polybasic organic acids which adjust the pH at the surface of the erodible matrix to accelerate or retard the decomposition of the polymer in the gastric or intestinal environment.

In a further example, Sothmann, et al., in U.S. Pat. No. 4,351,825, disclose a sustained release oral dosage form wherein a drug is dispersed in a matrix of a water-insoluble polymethacrylate, e.g., a copolymer of acrylic and methacrylic acid esters containing quaternary ammonium groups or a copolymer of methacrylic acid and methyl methacrylate, which has an anionic character. The granules of the matrix material are mixed with the active drug and an erosion rate modifier which is an ester of a long chain fatty acid with glycerine or a long chain alcohol.

Additionally, Kleber, et al., in U.S. Pat. No. 4,333,919, disclose controlled release formulations comprised of a drug mixed with a copolymer of lactic and glycolic acids. The formulations may also contain adjuvants such as glyceryl distearate. The formulations are primarily intended for growth stimulants for ruminants. Accordingly, they are administered by filling open-ended steel cylinders with the formulations and placing the cylinders in the rumen of the animal. The filled steel cylinders remain in the rumen, and the growth stimulant is gradually released as the matrix is eroded by the rumen fluids.

It seems evident from these disclosures, and others, that the erodible formulations of the prior art have generally required specially prepared polymers, and that the rate of erosion of such polymers cannot always be adjusted to provide for preferential release of the drug in a particular portion of the gastrointestinal tract, e.g., in the stomach or small intestine.

Erodible matrix formulations based on mixtures of polyethylene glycols specially adapted for buccal dosage forms have been disclosed by Keith et al, U.S. Pat. No. 4,764,378. An erodible matrix suitable for preparing pharmaceutical dosage forms for oral administration is disclosed in U.S. Pat. No. 4,629,621, the grandparent application of this application. and in U.S. Pat. No. 4,774,074, a continuation-in-part of U.S. Pat. No. 4,629,621. The compositions of those U.S. Patents comprise a polyethylene glycol or mixture thereof in combination with an insoluble amphiphile. Preferred compositions incorporating particular insoluble amphiphiles are disclosed in U.S. Pat. No. 4,774,976, to Snipes and Wagner, a continuation-in-part of U.S. Pat. No. 4,629,621. Preferred erodible compositions based on a mixture of one or more polyethylene glycols and a polyethylene oxide-polypropylene oxide block copolymer in combination with an insoluble amphiphile are disclosed in U.S. patent application No. 06/918,273, the parent application of this application.

However, while the erodible compositions disclosed in the parent applications and related applications have been found to be useful as controlled release matrices for many pharmaceutical compounds, certain drugs have presented problems in formulation. It has been found that some drugs, particularly those having melting points not far above room temperature, have a tendency to supercool when the molten drug is cooled to solidify it. When a sample of such a drug is melted by heating and then cooled to a temperature below its melting point, the material does not immediately solidify, but rather remains liquid for some time. Although the drugs eventually solidify, their tendency to supercool causes a problem when they are incorporated into the matrices disclosed in the the parent applications and related applications. Inasmuch as the dosage forms disclosed in those applications are prepared by melting together the ingredients of the matrix, adding the drug to the molten matrix and cooling the mixture in a mold, the supercooling tendency of these drugs, especially when they are present in relatively large proportion in the composition of the dosage form, prevents the dosage form from solidifying properly. In addition, some drugs having comparatively high melting points dissolve to some extent in the molten matrix and cause the matrix itself to exhibit delayed solidification upon cooling. Evidently, dosage forms which have not solidified cannot be removed from the mold and subjected to the handling necessary to package them.

Therefore, a need has continued to exist for an erodible matrix, prepared from readily available materials which are suitable for sustained release pharmaceutical formulations, wherein the rate of erosion can be substantially controlled and which is capable of forming a solid mixture with drugs which are subject to supercooling.

SUMMARY OF THE INVENTION

Accordingly, it is an object of this invention to provide an oral, sustained release dosage form.

A further object is to provide an oral, sustained release dosage form incorporating an erosion rate modifier substance.

A further object is to provide an oral, sustained release dosage form whose formulation and/or structure can be adjusted to release its medication either in the stomach or the small intestine.

A further object is to provide a sustained release composition containing a bioactive compound which is released by erosion of the matrix in an aqueous liquid environment.

A further object is to provide a liquid-erodible composition which is capable of forming a solid dosage form in the presence of relatively large amounts of a drug which is subject to supercooling.

Additional objects will become apparent from the description of the invention which follows.

The objects of the invention are achieved by a sustained release composition for releasing a biologically active compound into its surrounding environment comprising said biologically active compound being dispersed in a matrix which, when contacted with an aqueous liquid, erodes progressively, said matrix having a melting point lower than that of said biologically active compound, and said matrix comprising a.) about 5% to 100% by weight of a solid water-dispersible polyether diol having a molecular weight from about 1000 to about 20,000, selected from the group consisting of polyethylen glycols and polyethylene oxide-polypropylene oxide block copolymers, and b.) about 95% to 0% by weight of an erosion rate modifier which is an amphiphilic compound insoluble in the aqueous liquid and having a hydrophobic portion and a hydrophilic portion.

DETAILED DESCRIPTION OF THE INVENTION AND PREFERRED EMBODIMENTS

The property of the composition of this invention which makes it useful in sustained release preparations of bioactive material is its erodible character. Because it is the surface of an erodible composition which dissolves or decomposes into the surrounding medium and the eroding liquid does not substantially penetrate its structure, it is possible to achieve superior control of the dissolution rate of the solid composition, so that it may be used in a variety of applications.

In addition, by selecting the ingredients of the matrix of this invention so that the melting point of the matrix is less than that of the biologically active compound dispersed in the matrix it is possible to overcome a problem which occurs when compounds which have a tendency to supercool are to be incorporated into the matrix. As pointed out above, certain compounds have a tendency, when cooled from the molten state to a temperature below their melting point, to remain in the liquid state for a time instead of promptly crystallizing when the melting point is reached. While the invention is applicable to the preparation of dosage forms for any biologically active compound which has a tendency to supercool, it is especially adaptable to the preparation of dosage forms incorporating relatively low melting drugs, i.e., those having melting points from about 40° C. to 100° C. which also have a tendency to supercool.

Dosage forms comprising a biologically active compound dispersed in an erodible matrix of polyether diols have conventionally been prepared by melting the matrix ingredients, e.g., at a temperature of 60° C. to 100° C., dispersing the biologically active compound in the molten matrix, and molding the dosage form by introducing the molten dispersion into a mold, e.g., by injection molding, and cooling the dispersion in the mold to form a solid dosage form. When a biologically active compound having a relatively low melting point, i.e., less than 100° C., and having a tendency to supercool is incorporated into the matrix by this process, molten droplets of the biologically active compound may be dispersed in the molten matrix, especially when the biologically active compound is not very soluble in the matrix. When the molten matrix is cooled, these dispersed droplets may not solidify, and the presence of the still-liquid droplets dispersed in the matrix prevents the resulting dosage form from solidifying properly in the mold. The dosage forms thus tend to stick to the mold, and, even if they are somehow removed from the mold, they do not retain their shape, but are easily deformed, even under their own weight. Furthermore, such molded articles remain sticky and adhere to one another and to surfaces which they may contact. The problem is especially acute with those biologically active compounds which are used in relatively large amounts in the dosage form, e.g., those compositions wherein the active ingredient may amount to 40% or more by weight of the final composition.

Certain biologically active compounds may also dissolve in the matrix of polyether diols and alter its properties so that the matrix itself does not solidify rapidly upon cooling. The use of a low-melting matrix in the composition of this invention also minimizes the amount of active compound which dissolves in the matrix and thus tends to prevent alteration of the properties of the matrix by dissolved active ingredient.

Biologically active compounds which exhibit the phenomenon of supercooling include gemfibrozil (M.P. 61°–63° C.), ibuprofen (M.P. 75°–77° C.), tulobuterol (M.P. 89°–91° C.), butylated hydroxytoluene (M.P. 70° C.), and acetaminophen (M.P. 169°–170.5° C.).

A preferred composition of the invention is especially suitable for incorporating a drug to be administered over a period of time via the intestinal absorption route. It is formed from a composition comprising solid water-dispersible polyether diol and an amphiphilic erosion rate modifier, and the kinetics of its drug release are determined by the properties of the matrix and the shape of the dosage form. Accordingly, the rate of release can be controlled by varying the size and shape of the dosage form as well as the proportion and type of the erosion rate modifier.

One particular dosage regimen wherein the controlled release composition of this invention is useful is in the administration of drugs which have a relatively short biological half-life in the body. Such drugs can be incorporated into a dosage form made from the erodible controlled release matrix of this invention which is designed to release the drug continuously over a period of 6 to 18 hours in order to provide a continuous supply of the drug to the patient and thereby maintain a therapeutic level of the drug in the patient. Such relatively long-lived dosage forms will have an erodible matrix of the invention which incorporates a relatively large amount of the release rate modifier, e.g., 60% to 20% by weight of the composition. Another dosage regimen which can make use of the controlled release matrix of this invention is found in the case of drugs which have a sufficient half-life, e.g., up to 18 hours, so that sustained release of the medication is not necessary to maintain a therapeutic level in the patients plasma or the target organ. However, when long-lasting drugs of this type are given in a dosage form which releases the medication all at once, the initial concentration of the drug in the patients bloodstream may exceed the therapeutic range and result in undesirable side effects. With such drugs it is desirable to control the rate of absorption to avoid an initial overdose, and release of the drug over a period of 30 minutes to two hours will accomplish this goal. For this relatively rapid, but controlled, release the amount of release rate modifier will be present in amounts of about 10% to about 0.5% by weight of the matrix The solid water-dispersible polyether diol used in the erodible matrix of this invention may be water-soluble or may be capable of being dispersed in water by the formation of micelles.

The solid water-dispersible polyether diol component of the erodible matrix of this invention may include any polyethylene glycol (PEG) having a molecular weight from about 1000 to about 20000. All of the polyethylene glycols in this range are solid materials which are soluble in water and which will slowly dissolve when in contact with an aqueous medium. Mixtures of polyethylene glycols of different molecular weights may also be used. A preferred matrix according to the invention is one having a melting point no greater than 60° C. and preferably about 55° C. Matrices having melting points in this temperature range will typically comprise PEG's having a molecular weight in the range of 3000 to 4000. A preferred PEG which may be used alone or in mixtures with other polyether diols is PEG having a molecular weight of about 3350.

Also suitable as solid water-dispersible polyether diols are block copolymers of polyethylene oxide and polypropylene oxide having the general formula

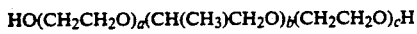

$$HO(CH_2CH_2O)_a(CH(CH_3)CH_2O)_b(CH_2CH_2O)_cH$$

wherein b has a value of 15 or greater and the sum of a and c may vary so that these terminal portions of the molecule may comprise from 20% to 90% by weight of the polymer molecule. The molecular weights of these block copolymers may range from 1000 to 16000 or more. The properties of these block copolymers may vary substantially depending on the molecular weight and the ratio of a+b to c. Those block copolymers of the above formula which are solid at room temperature and which are water-dispersible are included among the solid water-dispersible polyether diols useful in this invention. Block copolymers of this type are available from a number of manufacturers. Preferred block copolymers of this type are those having a melting point not greater than about 60° C. and more preferably those having a melting point not greater than about 55° C. Preferred block copolymers are those having a molecular weight of about 6000 to 14,000.

The polyether diol component of the preferred embodiment of the erodible matrix of the composition of this invention may be present in amounts ranging from about 5% to 100% by weight of the matrix. When a relatively slow release composition is desired, the proportion of the polyether diol component will range from about 40% to about 80% by weight of the matrix, while when a relatively rapid controlled release is desired, the proportion of the polyether diol component will be from about 90% to 100% by weight of the matrix.

In a preferred embodiment of the invention the erodible matrix includes an effective amount of an erosion rate modifier which has the effect of adjusting the rate of erosion of the matrix under the conditions found in the gastrointestinal tract. The erosion rate modifier used in the preferred embodiment of the erodible matrix is an insoluble amphiphile, that is, a material whose molecule possesses a hydrophilic portion and a lipophilic portion, usually located at opposite ends of a relatively elongated molecule. The presence of lipophilic portions in the erosion rate modifier slows down the rate at which the matrix is eroded when in contact with an aqueous liquid environment. Therefore, the rate of erosion can be slightly retarded by incorporating relatively small amounts of erosion rate modifier and greatly retarded by incorporating relatively large amounts of erosion rate modifier.

The erosion rate modifier can also be chosen to vary the rate of erosion under varying conditions of pH. For example, if the erosion rate modifier is a long chain fatty acid such as myristic acid, the erosion rate of the matrix will be relatively slow in acid media wherein the carboxyl group of the myristic acid is not ionized and the amphiphilic molecule is accordingly relatively hydrophobic. On the other hand, under basic conditions the carboxyl group is ionized, and therefore hydrophilic, which makes the erosion rate considerably faster. Evidently, a dosage form made from such a formulation releases relatively little of a drug in the acidic environment of the stomach, but subsequently more freely releases the drug in the basic environment of the small intestine. In the event that erosion of the matrix in the stomach is desired, then erosion rate modifiers having basic groups which are ionized under acidic conditions can be incorporated in the matrix composition.

The erosion rate modifier can also be chosen to compensate for the effects of charged forms of the bioactive compound on the erosion rate. When the bioactive compound, e.g., a drug, is present in the matrix of the invention in amounts greater than about 2-3% by weight of the total composition, the ionic character of the drug can affect the rate of erosion at various pH's of the eroding environment. For, example if the erodible matrix contains a basic drug, which will assume a positive charge in the acidic environment of the stomach, thereby increasing the erosion rate, an acidic erosion rate modifier, e.g., a long chain fatty acid such as myristic acid, may be used as an erosion rate modifier. The acid will remain un-ionized in the acidic environment of the stomach and thereby act to retard the erosion rate and counterbalance the effect of the basic drug.

Use of erosion rate modifiers devoid of ionizable hydrophilic groups, such as long chain aliphatic alcohols, results in an erodible matrix whose rate of erosion is not greatly affected by the pH o the environment.

The erosion rate modifier may be present in the matrix of the erodible compositions of this invention in amounts of about 95% to 0% by weight of the matrix. When a relatively slowrelease matrix is desired, the erosion rate modifier will preferably constitute about 60% to about 20% by weight of the matrix, while when a relatively rapid controlled release matrix is desired, the erosion rate modifier will be present in a proportion of about 10% to 0% by weight of the matrix.

Suitable erosion rate modifiers include $C_{12}$–$C_{20}$ fatty acids, such as lauric acid, myristic acid, palmitic acid, stearic acid, and arachidic acid; $C_{12}$–$C_{20}$ alcohols, such as lauryl alcohol, myristyl alcohol, palmityl alcohol, stearyl alcohol and arachidyl alcohol, amphiphilic esters of fatty acids with glycerol, particularly monoesters of $C_{12}$–$C_{20}$ fatty acids such as glyceryl monopalmitate, $C_{12}$–$C_{20}$ amines such as lauryl amine, myristyl amine, palmityl amine, stearyl amine and arachidyl amine, and amides of $C_{12}$–$C_{20}$ fatty acids.

In various dosage forms embodiments of this invention, the rate of drug release can be controlled by varying the shape of the dosage form or by coating the surface of the dosage form. For example, an erodible dosage form of the invention may have a cylindrical shape wherein the height of the cylinder is much greater than the diameter, so that most of the area of the cylinder exposed to the erosive action of the aqueous liquid medium is constituted by the curved peripheral surface of the cylinder. When such a cylinder is immersed in a liquid medium the peripheral surface of the cylinder will be eroded. As the diameter of the cylinder decreases through its erosion, the area of the peripheral surface exposed to the erosive action of the aqueous liquid environment decreases proportionally. Therefore, the dosage form will erode at a rate which will provide approximately first order drug release kinetics. If a cylindrical dosage form has a relatively small height compared with its diameter, so that most of the exposed area is provided by the bases of the cylinder, the eroding surface area of the dosage form will not change greatly as erosion proceeds. In this case the rate of drug release will be substantially constant, i.e., the drug release kinetics will be approximately zero order.

In another embodiment, the surface of the dosage form can be partially coated with a liquid-impervious coating so that only certain surfaces of the dosage form are exposed to the erosive action of the medium. This method also allows for adjusting the kinetics of drug release. For example, if a cylindrical dosage form is coated on its curved peripheral surface so that only the ends of the cylinder are exposed to the erosive action of the medium, the area of the dosage form exposed to erosive action will not change with time. In this embodiment, therefore, the drug will be released at a constant rate, i.e., the release kinetics will be approximately zero order.

In order to assure that the rate of drug release will actually remain substantially constant for this coated cylindrical dosage form, it is necessary that the coating be non-self-supporting. If the coating is self-supporting it will extend beyond the ends of the cylindrical portion remaining after a portion of the dosage form has been eroded. This extension will interfere with the access of the eroding aqueous liquid medium to the ends of the cylinder and will, accordingly, affect the kinetics. Therefore, the preferred coating for this type of dosage form is a very thin friable material which is not self-supporting. With such a coating, any portion extending beyond the end of the cylinder after the immediately underlying matrix has been eroded will be broken off as the dosage form is subjected to agitation in the gastrointestinal tract, thus keeping the uncoated ends of the cylinder fully exposed to the erosive action of the medium.

In most cases it will be convenient to apply the coating material in the form of a melt which solidifies by cooling on the surface of the dosage form. Preferred coating materials are long chain fatty acids having 12 to 20 carbon atoms. Such acids include lauric acid, myristic acid, palmitic acid, stearic acid and arachidic acid. The thickness of the coating will typically be from about 0.02 mm to about 0.5 mm.

Additional ingredients can be incorporated into the erodible composition of this invention to modify and/or control the properties of the composition. For example, in order to improve the compatibility between the polyethylene glycol and the erosion rate modifier and prevent phase separation when the molten composition is cooled, a modified polyethylene glycol wherein the OH groups at one or both ends are esterified with long chain fatty acids may be added to the mixture. Suitable long chain fatty acids are aliphatic fatty acids having from about 12 to about 20 carbon atoms such as those disclosed above. Preferred polyethylene glycols to be used in preparing the esterified PEG compatibility enhancers are those having a molecular weight from about 200 to 10000, preferably from about 200 to about 200 0. PEG 400 and PEG 600 are particularly preferred materials for preparing the esterified PEG's. For example, the esterified PEG's may be the monoesters and preferably the lauric or stearic ester. More preferred esters are the diesters, particularly the dilauroyl and distearoyl esters. These modified polyethylene glycols are prepared by conventional esterification procedures well known to those skilled in the art, such as reacting the polyethylene glycol with the acid chloride of the chosen acid. The modified polyethylene glycol may be incorporated into the compositions of this invention in any effective amounts, such as in an amount up to about 10% by weight, preferably from about 0.1% to about 10% by weight, and particularly about 2% by weight.

Starch may also be added to the erodible mixture of this invention as a disintegrant in order to adjust the erosion rate. The starch tends to enhance the erodible characteristics of the composition by causing the solid material to dissolve from the surface without penetration of the aqueous liquid into the interior of the solid form. Any type of starch may be used, particularly a pharmaceutically acceptable and readily available form of starch, such as cornstarch. Starch may be present in amounts of from about 5% by weight to about 60% by weight, preferably from about 10% by weight to about 50% by weight, and more preferably from about 20% by weight to about 40% by weight.

Molding adjuvants may also be added to the compositions of this invention. It has been found that the addition of a polyethylene oxide (PEO) having a molecular weight (MW) from about 100,000 to about $5—10^6$ has beneficial effects on the viscosity and plasticity of the composition. This provides for easier mold filling and release of molded forms from the molds, especially when molded dosage forms of this invention are prepared by injection molding. The PEO may be present in an effective amount up to about 2% by weight, preferably from about 0.05% by weight to about 1% by weight, and most preferably about 0.1% by weight. It will be appreciated by those skilled in the art that injection molding of compositions containing a relatively large number of ingredients, such as the compositions of this invention, is not common. Hence, some experimentation may be required to determine the exact amount of molding adjuvant needed for a given composition.

Another molding adjuvant which may be added to the matrix of the dosage form of this invention is hydroxypropyl methylcellulose, which may be added in amounts up to about 11% by weight of the matrix. The addition of hydroxypropyl methylcellulose provides somewhat improved mold release properties to the molded dosage form. The hydroxypropyl methylcellulose may also incorporate a pharmaceutically acceptable coloring agent to impart a color to the dosage form. The amount of hydroxypropyl methylcellulose may range up to about 12% by weight of the matrix.

Another molding adjuvant which may be included in the compositions of this invention is colloidal silica, which may be included in the composition in an amount up to 3% by weight of the matrix, preferably about 1% by weight. Increasing amounts of colloidal silica yield a harder dosage form.

For water-soluble drugs and bioactive compounds, a preferred matrix which provides uniform release kinetics under conditions of varying pH and for a great many different drugs comprises a composition according to the invention wherein the release rate modifying agent is a combination of stearyl alcohol and stearic acid. The amounts of stearyl alcohol may range from about 4% to about 13% by weight and the amount of stearic acid may range from about 4% to about 15% by weight. It is also preferred in this composition to include up to about 45% by weight of a hydratable material which serves to increase the rate at which water penetrates into the composition to dissolve the water soluble or water-dispersible components, i.e., the PEG's, polyethylene oxide-polypropylene oxide block copolymers, drugs, and the like. Such hydratable materials include starch, e.g., corn starch, and colloidal silica. It is also preferred that this composition incorporate a long chain aliphatic monoester of a PEG having a molecular weight of about 400, e.g., PEG 400 monostearate, in amounts of about 2% to about 8% by weight in order to improve the compatibility of the PEG with the amphiphilic erosion rate modifier as discussed above.

In addition to the use of PEG (400) monostearate or another long chain aliphatic monoester of PEG to improve the compatibility of the PEG with the amphiphile erosion rate modifier in the matrix, PEG (400) monostearate is also useful as an erosion rate modifier when used in conjunction with amphiphilic erosion rate modifiers, e.g., a fatty acid or fatty alcohol, or the preferred combination of stearic acid and stearyl alcohol. The amount of PEG (400) monostearate required to function as an erosion rate modifier may range from 2 to 8% by weight.

Another ingredient which may be incorporated into a preferred embodiment of this invention is a nonionic surfactant, which may be present in an amount ranging from 0% to about 5% by weight of the matrix. The nonionic surfactant, if present, acts as a wetting agent and helps to produce a more uniform and reproducible erosion rate. The surfactant can also be incorporated for the purpose of increasing the rate of erosion of the matrix.

The erodible composition of this invention may also contain an ecological agent dispersed therein in order to provide for gradual release of the ecological agent into an aqueous liquid environment. An ecological agent is defined for purposes of this invention as a non-pharmaceutical substance which has a biological effect on plants or animals in the environment. An ecological agent may be a pesticide, such as an insecticide or herbicide, a fertilizer, a pheromone, a plant growth hormone, or the like. When dosage forms made from compositions containing such bioactive ingredients contact an aqueous liquid environment the bioactive materials are gradually released into the environment. Accordingly, the compositions of this invention are useful for releasing such ecological agents into bodies of water or into a land environment where they may release their active agents by contact with rain or standing water, so as to maintain an effective concentration of the agent in the environment for a relatively long period of time.

It is preferred to use the erodible matrix of this invention as a carrier for sustained release pharmaceuticals administered orally to individuals in need of a relatively constant concentration of medication. The drugs may be locally or systemically acting drugs, and may be selected from among any group wherein a steady concentration of the drug in the organism is desired. Accordingly, the drug may be selected from among analgesic, anorexic, antiarthritic, antibacterial, antibiotic, anticonvulsant, anti-depressant, antidiabetic, anti-fungal, antihistaminic, anti-hypertensive, anti-inflammatory, anti-neoplastic, antiparkinsonism, antipyretic, anticholinergic, anti-inflammatory, anesthetic, antimicrobial, antiviral, anti-ulcer, bronchodilator, cardiovascular, contraceptive, central nervous system affecting, inotropic, vasodilator, vasoconstrictor, decongestant, diuretic, hypoglycemic, hormone, hypnotic, hematinic, electrolyte supplement, germicidal, muscle relaxant, parasympatholytic, parasympathetomimetic, tranquilizer, ophthalmic, psychostimulant, vitamin, and the like drugs. The drugs can be administered in the form of the parent compound as well as in the form of pharmaceutically acceptable salts, and precursors.

Preferred drugs for use in the dosage forms prepared according to the invention include gemfibrozil, ibuprofen tulobuterol and acetaminophen. Butylated hydroxytoluene is a biologically active compound having a tendency to supercool which may be incorporated into the compositions of this invention.

The proportions of drug and erodible matrix in the dosage forms of this invention may vary within wide limits. However, the problems associated with supercooling of the pharmaceutical compound are most prominent when the compound is present in relatively large amounts, e.g., 40% by weight of the composition or more. The amount of active ingredient may range up to about 75% by weight of the composition or more, with the balance being the erodible matrix.

While the unit dosage forms of the invention can be prepared by conventional procedures such as compression molding, tableting, extrusion, and the like, the compositions of the invention are particularly suited for preparing dosage forms by injection molding. It is preferred that the dosage forms of the invention be non-porous in order that the erosion will proceed from the surface of the dosage form. Such non-porous dosage forms are best prepared by solidification of a molten form of the composition containing all ingredients of the composition, and injection molding is especially useful for that purpose. Indeed, the dosage forms of the invention are especially adapted to production by injection molding because the erodible matrix composition of the invention has a relatively low melting temperature, and hence the injection molding can be carried out at a temperature which is not detrimental to the drug contained in the dosage form.

The preferred dosage forms of the invention have a cylindrical shape with a diameter of about 3 mm to about 8 mm, and preferably about 5 mm. The length of the cylindrical dosage form is typically about 5 mm to about 20 mm, and is preferably about 10 mm. The preferred dosage forms may be coated on their peripheral cylindrical surfaces with a liquid-impervious non-self-supporting coating as discussed above.

The sustained release compositions of this invention are prepared by the following general procedure.

A premeasured amount of a polyether diol, e.g, a polyethylene glycol or a polyethylene oxide-polypropylene oxide block copolymer or mixtures thereof, is melted in a vessel, e.g., a kettle provided with a steam jacket or a heating mantle and equipped with a stirring mechanism. A temperature of about 85° C. is sufficient to melt any of the polyethylene glycols. However, the polyether diol or mixture thereof must be chosen to have a melting point lower than that of the active pharmaceutical compound to be incorporated into the mixture. Inasmuch as polyethylene glycols and polyethylene oxide-polypropylene oxide block copolymers ar commercially available in a wide range of molecular weights with a correspondingly wide range of melting points, the selection of a suitable polyether diol or mixture thereof is readily accomplished. It is preferred to use a mixture of polyether diols which has a melting point in the range of 45°-50° C. Such a melting point is lower than that of most drugs of interest, but still high enough that the dosage forms prepared therefrom are unlikely to melt when exposed to the temperature extremes experienced in storage and shipping. If a water-insoluble amphiphile is to be incorporated into the matrix of the invention, a premeasured amount of the amphiphile is added either as a molten liquid or as a solid. It is preferred to add the insoluble amphiphile slowly to the stirred molten PEG. The long chain fatty amphiphiles useful in the compositions of this invention are generally molten at the temperature of the molten PEG and can be readily mixed with the PEG. Other ingredients, such as disintegrants (e.g., starch), molding adjuvants (e.g., polyethylene oxide), and the like are then added and the mixture is thoroughly blended. The bioactive agent, drug or the like is then added in the form of a finely divided powder and mixed thoroughly with the molten mixture. Dosage forms may then be formed directly from the molten mixture by the procedures outlined above.

In an alternative method of preparation, the ingredients of the matrix are melted and blended together in the absence of the active ingredient. The matrix is then solidified by cooling and granulated, e.g., by mechanical impact. The pharmaceutical compound in finely divided form is then thoroughly mixed with the granulated solid matrix and the mixture is fed into the hopper of a conventional injection molding machine equipped with an injection cylinder which can be heated to a temperature above the me ting point of the matrix. The granulated mixture is forced through the injection cylinder, where the matrix becomes molten, and into the mold where the composition is solidified. This procedure allows little time for a pharmaceutical compound which might be soluble in the molten matrix to dissolve therein and adversely effect the solidification properties of the matrix.

The invention will now be further elucidated by the following examples which are included by way of illustration only and are not intended to be limiting. In the examples all percentages and parts are weight unless otherwise specified.

EXAMPLE 1

This example illustrates the preparation of dosage forms of the invention having a matrix of a polyethylene oxide-polypropylene oxide block copolymer A series of compositions was prepared by the general procedure described above. A molten mixture of a polyethylene oxide-polypropylene oxide block copolymer having a melting point of about 45° C. and a water insoluble amphiphile component was prepared, and the drug gemfibrozil, in finely divided form, was dispersed in the molten mixture. The molten dispersion was cooled to room temperature and the solid was granulated by mechanical impact. The granulated composition was fed into the hopper of a conventional injection molding machine having a heated cylinder heated to a temperature just hot enough to melt the composition, and the molten composition was injected into molds and cooled therein. The dosage forms were of the general shape of a pharmaceutical capsule, having a length of about 18 mm and a diameter of 5 mm, and a weight of about 815 milligrams.

The compositions of the dosage forms are tabulated in Table I.

TABLE I

| Ingredient | Composition (% by weight) | | | | | | |
|---|---|---|---|---|---|---|---|
| | A | B | C | D | E | F | G |
| polyethylene oxide-polypropylene oxide block copolymer (MW 11,400) | 17 | 15 | 17 | 18 | 19 | 22.5 | 24.5 |
| polyethylene glycol 400 monostearate | 5 | 4 | 5 | 5 | 4.5 | 4 | 3 |
| myristic acid | — | — | — | — | 0.5 | 0.5 | 0.5 |
| hydroxypropyl methylcellulose (uncolored) | 8 | 11 | — | — | 2 | 2 | 2 |
| hydroxypropyl methylcellulose (colored) | — | — | 9 | 7 | 5 | 2 | 1 |
| colloidal silica | 2 | 2 | 1 | 2 | 1 | 1 | 1 |
| gemfibrozil | 68 | 68 | 68 | 68 | 68 | 68 | 68 |

The dosage forms of this example were easy to remove manually from the experimental mold and did not adhere to the metal surface of the mold. The molded dosage forms were firm, hard, non-sticky, and resistant to crushing.

The sustained release properties of the dosage forms were then tested by the following procedure:

Simulated intestinal fluid (SIF) was prepared by the following procedure:

1) 6.8 grams of monobasic potassium phosphate were dissolved in 250 ml of water.

2) 190 ml of 0.2 N NaOH was added with stirring.

3) 400 ml of water and 10 ml of pancreatin were added.

4) The pH of the solution was adjusted with 0.2 N NaOH to 7.5±0.1.

5) The solution was diluted with water to 1000 ml.

The dissolution kinetics were determined by allowing the dosage form to be tested to dissolve in about 900 milliliters of SIF at 37° C. in the standard dissolution testing Apparatus 2 of the United States Pharmacopoeia (United States Pharmacopoeia, Twenty-first Revision, U.S. Pharmacopoeial Convention, Inc., Rockville, Maryland, 1985, pp. 1243-1244). The amount of drug released was monitored by periodically measuring the optical density of the aqueous medium at an absorption peak of gemfibrozil using an ultraviolet spectrophotometer. Each of the dosage forms was found to release the drug gradually over a period of several hours.

EXAMPLE 2

This example illustrates a formulation using a mixture of polyethylene glycols and a polyethylene oxide-polypropylene oxide block copolymer.

A series of compositions was prepared by the general procedure of Example I, using a matrix comprising a mixture of polyethylene glycols, a polyethylene oxide-polypropylene oxide block copolymer a water-insoluble amphiphile component, and auxiliary ingredients, the matrix having a melting point of about 45° C. The drug gemfibrozil, in finely divided form, was dispersed in the molten mixture. The molten dispersion was injection molded into dosage forms of the size and shape prepared in Example 1.

The compositions of the dosage forms are tabulated in Table II.

TABLE II

| Ingredient | Composition (% by weight) | | | | | |
|---|---|---|---|---|---|---|
| | A | B | C | D | E | F |
| PEG 1450 | 7 | — | — | — | — | — |
| PEG 3350 | 6.5 | 10 | 13 | 14 | 13.7 | 13.4 |
| polyethylene oxide-polypropylene oxide block copolymer (MW 12,600) | 10 | 10 | 8.75 | 10 | 10 | 10 |
| polyethylene glycol 400 monostearate | 3 | 3 | 3 | 3 | 3 | 3 |
| myristic acid | 0.5 | 0.5 | 1 | 1 | 1 | 1 |
| hydroxypropyl methylcellulose (uncolored) | 2 | 3 | 2 | 2 | 2 | 2 |
| hydroxypropyl methylcellulose (colored) | 1 | 1.5 | 1 | 1 | 1 | 1 |
| nonionic surfactant | 1 | 1 | 1 | — | 0.3 | 0.6 |
| colloidal silica | 1 | 2 | 1 | 1 | 1 | 1 |
| gemfibrozil | 68 | 68 | 68 | 68 | 68 | 68 |

The dosage forms were tested by the procedure of Example 1 and were found to release the drug over a period of several hours at a relatively constant rate.

EXAMPLE 3

This example illustrates dosage forms of the invention prepared by a preferred molding process.

Dosage forms of the invention were prepared by first preparing a granulated composition containing all the ingredients of the matrix but containing none of the pharmaceutical compound. This composition was prepared by the general procedure of Example 1, by melting the polyethyer diol components in a heated vessel and adding the other ingredients of the matrix with stirring until a uniform dispersion was obtained. This material was then solidified by cooling and granulated by conventional procedures. The finely divided matrix composition was then mixed thoroughly with the pharmaceutically active compound and the mixture was fed into the hopper of a conventional experimental injection molding machine equipped with an injection cylinder capable of being heated to a temperature above the melting temperature of the matrix composition and a multiple-cavity mold designed to produce molded cylindrical dosage forms in the shape of conventional pharmaceutical capsules having a length of about 18 mm and a diameter of about 5 mm. The injection cylinder was heated to a temperature above the melting point of the matrix composition but below the melting point of the pharmaceutical compound. The injection molding machine was then operated to force the granulated mixture of matrix and active ingredient through the injection cylinder and into the mold. The matrix wa melted in the cylinder and the mixture of pharmaceutical compound dispersed in the molten matrix was forced into the mold cavities, where it was solidified by cooling the mold. The mold was then opened and the molded dosage forms removed. The compositions of the dosage forms are tabulated in Table III.

TABLE III

| Ingredient | Composition (% by weight) | | | | |
|---|---|---|---|---|---|
| | A | B | C | D | E |
| PEG 3350 | 14 | 13.75 | 12.03 | 10 | 20 |
| polyethylene oxide-polypropylene oxide block copolymer (M.W. 12,600) | 10 | 10 | 10 | 10 | — |
| polyethylene glycol 400 monostearate | 3 | 3 | 2.62 | 3 | 3 |
| myristic acid | 1 | 1 | 0.874 | 1 | 0.5 |
| hydroxypropyl methylcellulose (uncolored) | 2 | 2 | 1.75 | 2 | 2 |
| hydroxypropyl methylcellulose (colored) | 1 | 1 | 0.874 | 1 | 2 |
| nonionic surfactant | — | 0.25 | 0.22 | 0.25 | 0.25 |
| colloidal silica | 1 | 1 | 0.874 | 0.25 | 0.25 |
| gemfibrozil | 68 | 68 | 72 | 73 | 72 |

The dosage forms so prepared were hard and nontacky. When tested for drug release behavior by the method of Example 1, they eroded with gradual release of the active ingredient.

EXAMPLE 4

This example illustrates the preparation of dosage forms of the invention containing ibuprofen.

Dosage forms of the invention were prepared by the general procedure of Example 3 containing the active ingredient ibuprofen instead of gemfibrozil. The dosage forms had the compositions tabulated in Table IV.

TABLE III

| Ingredient | Composition (% by weight) | | |
|---|---|---|---|
| | A | B | C |
| PEG 8000 | 10 | 15 | 7 |
| polyethylene oxide-polypropylene oxide block copolymer (MW 8,400) | 10 | 2 | — |
| polyethylene glycol 400 monostearate | 3 | 5 | 5 |
| glyceryl monostearate | — | — | 10 |
| hydroxypropyl methylcellulose (uncolored) | 2 | 5 | 5 |
| starch | 5 | 3 | 3 |
| ibuprofen | 70 | 70 | 70 |

The dosage forms so prepared were hard and nontacky. When tested for drug release by the method of Example 1, they eroded with gradual release of the active ingredient.

EXAMPLE 5

This example illustrates the preparation of a dosage form of this invention using acetaminophen, a drug which tends to dissolve in the matrix and produce a supercooling effect.

Dosage forms were prepared by the general procedure of Example 1 having the following composition:

| Ingredient | Composition (% by weight) |
| --- | --- |
| PEG 3350 | 14 |
| polyethylne oxide-polypropylene oxide block copolymer (MW 12,600) | 10 |
| polyethylene glycol 400 monostearate | 3 |
| myristic acid | 0.5 |
| hydroxypropyl methylcellulose (uncolored) | 2 |
| colloidal silica | 0.5 |
| acetaminophen | 70 |

The ingredients of the matrix were melted at 70° C. and the acetaminophen was added in powdered form and thoroughly mixed therewith. The mixture was then solidified by cooling and granulated by mechanical impact. The granulated composition was fed into the hopper of an injection molding machine and dosage forms were molded as described in Example 1. The molded dosage form were tested for dissolution in water at 37° C. using the U.S. Pharmacapoeia dissolution testing apparatus 2 as described in Example 1, and were found to erode gradually over a period of 30 minutes.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A sustained release composition for releasing a biologically active compound into an aqueous liquid environment comprising a biologically active compound dispersed in a matrix which, when contacted with an aqueous liquid, erodes progressively, said matrix having a melting point below that of said biological compound and said matrix comprising a mixture of
   a.) 5% to 100% by weight of a solid water-dispersible polyether diol having a molecular weight from about 1000 to about 20,000, selected from the group consisting of polyethylene glycols and polyethylene oxide-polypropylene oxide block copolymers, and
   b.) 95% to 0% by weight of an erosion rate modifier which is an amphiphilic compound insoluble in said aqueous liquid, the molecular structure of said amphiphilic compound having a lipophilic portion and a hydrophilic portion.

2. The composition of claim 1 wherein the melting point of said matrix is not greater than 50° C.

3. The composition of claim 2 wherein the melting point of said matrix is about 45° C.

4. The composition of claim 1 wherein said polyether diol is a polyethylene glycol having a molecular weight of about 3350.

5. The composition of claim 1 wherein said water-dispersible polyether diol is a block copolymer of ethylene oxide and propylene oxide.

6. The composition of claim 5 wherein said polyether diol is a block copolymer having the formula

wherein b has a value of 15 or greater and the sum of a and c is selected so that the terminal portions of the molecule comprise from 20% to 90% by weight of the polymer molecule.

7. The composition of claim 6 wherein said block copolymer has a molecular weight of 11,000–13,000 and a melting point between 50° C. and 60° C.

8. The composition of claim 1 wherein said erosion rate modifier is a $C_{12}$–$C_{20}$ fatty acid.

9. The composition of claim 8 wherein said fatty acid is selected from the group consisting of myristic acid and stearic acid.

10. The composition of claim 1 wherein said erosion rate modifier is a combination of stearyl alcohol and stearic acid.

11. The composition of claim 10 wherein said stearyl alcohol is present in an amount of about 4% to about 8% by weight and said stearic acid is present in an amount of about 4% to about 13% by weight.

12. The composition of claim 1 additionally comprising a substance which increases the compatibility of the polyethylene glycol and the erosion rate modifier.

13. The composition of claim 12 wherein said substance is a polyethylene glycol having a molecular weight from about 200 to about 10000 and having at least one of its terminal OH groups esterified with a $C_{12}$–$C_{20}$ fatty acid.

14. The composition of claim 13 wherein said polyethylene glycol is polyethylene glycol 400.

15. The composition of claim 13 wherein said substance is polyethylene glycol 400 having at least one of its terminal OH group esterified with stearic acid.

16. The composition of claim 1 additionally comprising a disintegrant.

17. The composition of claim 16 wherein said disintegrant is starch.

18. The composition of claim 1 additionally comprising a nonionic surfactant

19. The composition of claim 1 additionally comprising a molding adjuvant.

20. The composition of claim 19 wherein said molding adjuvant is polyethylene oxide having a molecular weight of 100,000 to 5,000,000.

21. The composition of claim 19 wherein said molding adjuvant is hydroxypropyl methylcellulose.

22. The composition of claim 19 wherein said molding adjuvant is colloidal silica.

23. A sustained release composition for releasing a biologically active compound into an aqueous liquid environment comprising a pharmaceutically active compound or non-toxic pharmaceutically acceptable salt of said pharmaceutically active compound dispersed in a matrix which, when contacted with an aqueous liquid, erodes progressively, said matrix having a melting point below the melting point of said pharmaceutically active compound or salt thereof and said matrix comprising a mixture of a.) 5% to 100% by weight of a solid water-dispersible polyether diol having a molecular weight from about 1000 to about 20,000, selected from the group consisting of polyethylene glycols and polyethylene oxide-polypropylene oxide block copolymers, and b.) 95% to 0% by weight of an erosion rate modifier which is an amphiphilic compound insoluble in said aqueous liquid, the molecular structure of said amphiphilic compound having a lipophilic portion and a hydrophilic portion.

24. The composition of claim 23 wherein said biologically active compound is gemfibrozil.

25. The composition of claim 23 wherein said biologically active compound is ibuprofen.

26. The composition of claim 23 wherein said biologically active compound is tulobuterol.

27. The composition of claim 23 wherein said biologically active compound is acetaminophen.

28. A sustained release dosage form for releasing a biologically active compound into an aqueous liquid environment comprising a non-porous solid erodible matrix having dispersed therein a biologically active compound, said matrix having a melting point lower than the melting point of said biologically active compound and said matrix comprising a mixture of a.) 5% to 99.5% by weight of a solid water-dispersible polyether diol having a molecular weight from about 1000 to about 20,000, selected from the group consisting of polyethylene glycols and polyethylene oxide-polypropylene oxide block copolymers, and b.) 95 to 0.5% by weight of an erosion rate modifier which is an amphiphilic compound insoluble in said aqueous liquid, the molecular structure of said amphiphilic compound having a lipophilic portion and a hydrophilic portion.

29. The dosage form of claim 28 wherein the melting point of said matrix is not greater than 50° C.

30. The composition of claim 29 wherein the melting point of said matrix is about 45° C.

31. The dosage form of claim 28 wherein said polyether diol is a polyethylene glycol having a molecular weight of about 3350.

32. The dosage form of claim 28 wherein said water-dispersible polyether diol is a block copolymer of ethylene oxide and propylene oxide.

33. The dosage form of claim 32 wherein said polyether diol is a block copolymer having the formula

HO(CH$_2$CH$_2$O)$_a$(CH(CH$_3$)CH$_2$O)$_b$(CH$_2$CH$_2$O)$_c$H wherein b has a value of 15 or greater and the sum of a and c is selected so that the terminal portions of the molecule comprise from 20% to 90% by weight of the polymer molecule 34. The dosage form of claim 33 wherein said block copolymer has a molecular weight of 11,000–13,000 and a melting point between 50° C. and 60° C.

35. The dosage form of claim 28 wherein said erosion rate modifier is a C$_{12}$–C$_{20}$ fatty acid.

36. The dosage form of claim 35 wherein said fatty acid is selected from the group consisting of myristic acid and stearic acid.

37. The dosage form of claim 28 wherein said erosion rate modifier is a combination of stearyl alcohol and stearic acid.

38. The dosage form of claim 37 wherein said stearyl alcohol is present in an amount of about 4% to about 8% by weight and said stearic acid is present in an amount of about 4% to about 13% by weight.

39. The dosage form of claim 28 additionally comprising a substance which increases the compatibility of the polyethylene glycol and the erosion rate modifier.

40. The dosage form of claim 39 wherein said substance is a polyethylene glycol having a molecular weight from about 200 to about 10000 and having at least one of its terminal OH groups esterified with a C$_{12}$–C$_{20}$ fatty acid.

41. The dosage form of claim 40 wherein said polyethylene glycol is polyethylene glycol 400.

42. The dosage form of claim 40 wherein said substance is polyethylene glycol 400 having at least one of its terminal OH groups esterified with stearic acid.

43. The dosage form of claim 28 additionally comprising a disintegrant.

44. The dosage form of claim 43 wherein said disintegrant is starch.

45. The dosage form of claim 28 additionally comprising a nonionic surfactant.

46. The dosage form of claim 28 additionally comprising a molding adjuvant.

47. The dosage form of claim 46 wherein said molding adjuvant is polyethylene oxide having a molecular weight of 100,000 to 5,000,000.

48. The dosage form of claim 46 wherein said molding adjuvant is hydroxypropyl methylcellulose.

49. The dosage form of claim 46 wherein said molding adjuvant is colloidal silica.

50. The dosage form of claim 28 wherein said biologically active compound is a pharmaceutically active compound or nontoxic pharmaceutically acceptable salt of said compound and said dosage form contains an effective amount of said compound or said salt.

51. The dosage form of claim 50 wherein said compound is gemfibrozil.

52. The dosage form of claim 50 wherein s id compound is ibuprofen.

53. The dosage form of claim 50 wherein said compound is tulobuterol.

54. The dosage form of claim 50 wherein said compound is acetaminophen.

55. The dosage form of claim 28 wherein said dosage form has the shape of a cylinder having hemispherical ends.

56. The dosage form of claim 55 wherein said cylinder has a diameter from about 3 mm to about 8 mm.

57. The dosage form of claim 56 wherein said cylinder has a diameter of about 6 mm.

58. The dosage form of claim 55 wherein said dosage form has a length from about 5 mm to about 20 mm.

59. The dosage form of claim 58 wherein said dosage form has a length of about 10 mm.

* * * * *